(12) United States Patent
McNair

(10) Patent No.: US 11,429,885 B1
(45) Date of Patent: Aug. 30, 2022

(54) COMPUTER-DECISION SUPPORT FOR PREDICTING AND MANAGING NON-ADHERENCE TO TREATMENT

(71) Applicant: CERNER INNOVATION, INC., Kansas City, KS (US)

(72) Inventor: Douglas S. McNair, Leawood, KS (US)

(73) Assignee: CERNER INNOVATION, North Kansas City, MO (US)

( * ) Notice: Subject to any disclaimer, the term of this patent is extended or adjusted under 35 U.S.C. 154(b) by 1006 days.

(21) Appl. No.: 15/851,517

(22) Filed: Dec. 21, 2017

Related U.S. Application Data

(60) Provisional application No. 62/437,655, filed on Dec. 21, 2016.

(51) Int. Cl.
  G06N 5/04    (2006.01)
  G06Q 30/02   (2012.01)
  G06F 17/18   (2006.01)
  G06N 20/00   (2019.01)
  G06N 7/00    (2006.01)
  G16H 10/60   (2018.01)
  G06N 7/08    (2006.01)

(52) U.S. Cl.
  CPC ............... G06N 7/005 (2013.01); G06N 7/08 (2013.01); G06N 20/00 (2019.01); G16H 10/60 (2018.01)

(58) Field of Classification Search
  CPC .......... G06N 7/005; G06N 20/00; G06N 7/08; G16H 10/60

USPC ....................................................... 706/1–62
  See application file for complete search history.

(56) References Cited

U.S. PATENT DOCUMENTS

| | | | |
|---|---|---|---|
| 10,098,582 B1 * | 10/2018 | McNair ................ | A61B 5/7264 |
| 2005/0209820 A1 * | 9/2005 | Inoue ................. | G05B 23/0232 |
| | | | 702/183 |
| 2005/0270024 A1 * | 12/2005 | Lin .................... | G01R 33/5611 |
| | | | 324/307 |
| 2007/0244738 A1 * | 10/2007 | Chowdhary ....... | G06Q 10/0637 |
| | | | 705/7.31 |
| 2013/0027561 A1 * | 1/2013 | Lee .................... | G06K 9/00302 |
| | | | 348/150 |
| 2013/0030875 A1 * | 1/2013 | Lee .................... | G06Q 30/0267 |
| | | | 705/7.38 |
| 2013/0191898 A1 * | 7/2013 | Kraft ..................... | G06F 21/31 |
| | | | 726/6 |
| 2014/0023253 A1 * | 1/2014 | Hesthaven ......... | G01R 33/5619 |
| | | | 382/131 |

(Continued)

Primary Examiner — Brandon S Cole
(74) Attorney, Agent, or Firm — Shook, Hardy & Bacon L.L.P.

(57) ABSTRACT

Technologies are provided for identifying individuals having a risk of non-adherence to or from a prescribed treatment program; for predicting and the risk, which may be determined as a forecast over a future time span; and evaluating it to further determine or invoke specific actions to mitigate the risk or otherwise improve likelihood of compliance. A singular spectrum analysis (SSA) is utilized to analyze temporal properties of a time series determined from measured or observational data to determine an emergent pattern. Based on this pattern, a risk of non-adherence, including relapse or absconding, over a future time interval by the individual may be determined and utilized to implement an intervening action.

18 Claims, 23 Drawing Sheets
(3 of 23 Drawing Sheet(s) Filed in Color)

(56) References Cited

U.S. PATENT DOCUMENTS

| | | | |
|---|---|---|---|
| 2015/0058388 A1* | 2/2015 | Smigelski | G06F 17/141 708/208 |
| 2016/0034615 A1* | 2/2016 | Heda | G06F 17/18 703/2 |
| 2016/0117466 A1* | 4/2016 | Singh | G06Q 50/265 702/19 |
| 2017/0147930 A1* | 5/2017 | Bellala | G06N 20/00 |
| 2018/0060151 A1* | 3/2018 | Gross | G06F 11/34 |

* cited by examiner

| ITEM | VALUE |
|---|---|
| SENSITIVITY | 95% |
| SPECIFICITY | 98% |
| EVENT PREVALENCE | 21% |
| POSITIVE PREDICTIVE VALUE (PPV) | 91% |
| NEGATIVE PREDICTIVE VALUE (NPV) | 99% |

| # | SSA INTERPRETATION | TIME SERIES | HETEROGENEITY MATRIX |
|---|---|---|---|
| 1 | TP – TEMP INCREASE IN DIMENSION, PARADIAGONAL BANDS | | |
| 2 | TP – TEMP INCREATE IN DIMENSION, PARADIAGONAL BANDS | | |
| 3 | UNCERTIAN; INCREASING DIMENSION | | |
| 4 | UNCERTIAN; INCREASING DIMENSION | | |
| 5 | TP – INCREASE IN DIMENSION, PARADIAGONAL BANDS | | |
| 6 | TP – INCREASE IN DIMENSION, PARADIAGONAL BANDS | | |
| 7 | UNCERTIAN; INCREASING DIMENSION | | |
| 8 | TN – INCREASING DIMENSION | | |

SSA PREDICTION EXAMPLES

*FIG. 4A.*

| # | SSA INTERPRETATION | TIME SERIES | HETEROGENEITY MATRIX |
|---|---|---|---|
| 9 | TN – INCREASING DIMENSION | | |
| 10 | UNCERTIAN; DECREASING DIMENSION | | |
| 11 | UNCERTIAN; DECREASING DIMENSION | | |
| 12 | UNCERTIAN; INCREASING DIMENSION | | |
| 13 | TN – NO CHANGE IN DIMENSION | | |
| 14 | TN – SEASONAL CHANGES IN DIMENSION | | |
| 15 | TN – SEASONAL CHANGES IN DIMENSION | | |
| 16 | TN – DECREASING DIMENSION | | |

SSA PREDICTION EXAMPLES

*FIG. 4B.*

```
###############################################################

#   Singular Spectrum Analysis For Gap and Changepoint Detection

######################################################### library(Rssa)

initialize decision threshold, offset, noise amplitude
thresh <- 0.57
off <- -1                                                              } 601
namp <- 0.08 use only terminal gap initiation load data - N=24, cp_idx=32, act=27 terminal, del=5
ts <- read.csv(file="c:/0_cerdstm/tP/gaps_freq_changepoint_detection/ts2.csv", header=TRUE,
colClasses="numeric")
ts <- as.ts(ts$ts)                                                     } 602
len <- length(ts)
# add gaussian noise to timeseries
ts <- ts + rnorm(len, 0.0, namp)
# set params for SSA                                                   } 603
L <- len %/% 2
B <- len %/% 2
T <- L                                                                 } 604
neig <- L %/% 2
# perform SSA
s <- ssa(ts, kind="1d-ssa", L=L, column.projector="centering", row.projector="centering")
# calculate factor vector of Hankel matrix, row detection fn           } 605
v2 <- round(abs(calc.v(s, 2)),2)
# detect changepoint (if any) and determine index of detected changepoint
if (length(which(v2 > thresh)) > 0){                                   } 606
  cp_idx <- L + min(which(v2 > thresh)) + off
  cp_idx                                                               } 607
}
# determine Hankel matrix
h <- hmatr(ts, L=L, B=B, T=T, neig=neig)                               } 608
# plot the Hankel matrix
h <- floor(1000*abs(h))
plot(h)
```

⋮

CONTINUES IN FIG. 6B

FIG. 6A

CONTINUES FROM FIG. 6A

```
# load data - N=32, cp_idx=32, act=29 terminal, del=3
ts <- read.csv(file="c:/0_cerdsm/itP/gaps_freq_changepoint_detection/ts3.csv", header=TRUE,
colClasses="numeric")
ts <- as.ts(ts$ts)
len <- length(ts)
# add gaussian noise to timeseries
ts <- ts + mvrnorm(len, 0.8, nsmp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
cp_idx <- L + min(which(v2 > thresh)) + off
cp_idx
}
# determine Hankel matrix
h <- hmatr(ts, L=L, B=B, T=T, neig=neig)
# plot the Hankel matrix
h <- floor(1000*abs(h))
plot(h)
```

```
# load data - N=32, cp_idx=nil, act=30 terminal, terminal zeroes too short (3)
ts <- read.csv(file="c:/0_cerdsm/itP/gaps_freq_changepoint_detection/ts4.csv", header=TRUE,
colClasses="numeric")
ts <- as.ts(ts$ts)
len <- length(ts)
# add gaussian noise to timeseries
ts <- ts + mvrnorm(len, 0.8, nsmp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
cp_idx <- L + min(which(v2 > thresh)) + off
cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6C

FIG. 6B

CONTINUES FROM FIG. 6B

```
# load data - N=32, cp_idx=32, act=29 terminal, del=3
ts <- read.csv(file="c:/fi_cerdsm/tP/gaps_freq_changepoint_detection/ts5.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(100f*abs(h))
plot(h)
```

```
# load data - N=32, cp_idx=nil, act=27 terminal, false-negative or terminal zeroes too short (6)
ts <- read.csv(file="c:/fi_cerdsm/tP/gaps_freq_changepoint_detection/ts6.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(100f*abs(h))
plot(h)
```

CONTINUES IN FIG. 6D

FIG. 6C.

CONTINUES FROM FIG. 6C

```
# load data - N=32, cp_idx=32, act=28 (terminal, del=4
ts <- read.csv(file="c:/0_cerdsm/IP/gaps_freq_changepoint_detection/ts7.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

```
# load data - N=32, cp_idx=nil, act=none, true-negative
ts <- read.csv(file="c:/0_cerdsm/IP/gaps_freq_changepoint_detection/ts8.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6E

FIG. 6D

CONTINUES FROM FIG. 6D

```
# load data - N=32, cp_idx=nil, act=none, true-negative
ts <- read.csv(file="c:/0_cerdsm/fP/gaps_freq_changepoint_detection/ts9.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

```
# load data - N=32, cp_idx=nil, act=none, true-negative
ts <- read.csv(file="c:/0_cerdsm/fP/gaps_freq_changepoint_detection/ts10.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6F

FIG. 6E

CONTINUES FROM FIG. 6E

```
# load data - N=32, cp_idx=nil, act=none, true-negative
ts <- read.csv(file="c:/0_cerdsm/IP/gaps_freq_changepoint_detection/ts11.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

```
# load data - N=32, cp_idx=nil, act=none, true-negative
ts <- read.csv(file="c:/0_cerdsm/IP/gaps_freq_changepoint_detection/ts12.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6G

FIG. 6F

CONTINUES FROM FIG. 6F

```
# load data - N=32, cp_idx=nil, act=none, true-negative
ts <- read.csv(file="c://0_cerdsm/IP/gaps_freq_changepoint_detection/ts13.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

```
# load data - N=32, cp_idx=nil, act=none, true-negative
ts <- read.csv(file="c://0_cerdsm/IP/gaps_freq_changepoint_detection/ts14.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6H

FIG. 6G

CONTINUES FROM FIG. 6G

```
# load data - N=32, cp_idx=nil, act=none, true-negative
ts <- read.csv(file="c://0_cerdsm/itP/gaps_freq_changepoint_detection/ts15.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

```
# load data - N=32, cp_idx=nil, act=none, true-negative
ts <- read.csv(file="c://0_cerdsm/itP/gaps_freq_changepoint_detection/ts16.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6I

FIG. 6H

CONTINUES FROM FIG. 6H

```
# load data - N=32, cp_idx=nil, act=none, true-negative
ts <- read.csv(file="c:/0_cerdism/IP/gaps_freq_changepoint_detection/ts17.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

```
# load data - N=32, cp_idx=nil, act=none, true-negative
ts <- read.csv(file="c:/0_cerdism/IP/gaps_freq_changepoint_detection/ts18.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

CONTINUES IN FIG. 6J

FIG. 6I

CONTINUES FROM FIG. 6I

```
# load data - N=32, cp_idx=nil, act=none, true-negative
ts <- read.csv(file="c://0_cerdsm/IP/gaps_freq_changepoint_detection/ts19.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

```
# load data - N=32, cp_idx=nil, act=none, true-negative
ts <- read.csv(file="c://0_cerdsm/IP/gaps_freq_changepoint_detection/ts20.csv", header=TRUE,
colClasses="numeric")
ts <- as.ts(ts$ts)
len <- length(ts)
# add gaussian noise to timeseries
ts <- ts + rnorm(len, 0.0, namp)
# set params for SSA
L <- len %/% 2
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
h <- floor(1000*abs(h))
plot(h)
```

FIG. 6J

```
########################################################
#    Singular Spectrum Analysis For Gap and Changepoint Detection
################################################## library(svd)
library(Rssa)

# initialize decision threshold and offset 0.36
thresh <- 0.44
off <- -1                                                                                  701 use only terminal gap initiation load data - N=24, cp_idx=31, act=27 terminal, del=4
ts <- read.csv(file="c://0_cerdsm/IP/gaps_freq_changepoint_detection/ts2.csv", header=TRUE,
colClasses="numeric")                                                                      702
ts <- as.ts(ts$ts)
len <- length(ts)
# add gaussian noise to timeseries
ts <- ts + rnorm(len, 0.0, 0.01)                                                           703
# set params for SSA
L <- len %/% 3
B <- len %/% 2                                                                             704
T <- L
neig <- L %/% 2
# perform SSA
s <- ssa(ts, kind="1d-ssa", L=L, column.projector="centering", row.projector="centering")  705
# calculate factor vector of Hankel matrix, row detection fn
v2 <- round(abs(calc.v(s, 2)),2)                                                           706
# detect changepoint (if any) and determine index of detected changepoint
if (length(which(v2 > thresh)) > 0){
  cp_idx <- L + min(which(v2 > thresh)) + off                                              707
  cp_idx
}
# determine Hankel matrix
h <- hmatr(ts, L=L, B=B, T=T, neig=neig)                                                   708
# plot the Hankel matrix
plot(h)
```

CONTINUES IN FIG. 7B

*FIG. 7A*

CONTINUES FROM FIG. 7A

```
# load data - N=32, cp_idx=nil, act=29 terminal, false-negative or terminal zeroes too short (4)
ts <- read.csv(file="c:/0_cerdsm/IP/gaps_freq_changepoint_detection/ts3.csv", header=TRUE,
colClasses="numeric")
ts <- as.ts(ts$ts)
len <- length(ts)
# add gaussian noise to timeseries
ts <- ts + mvrnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
cp_idx <- L + min(which(v2 > thresh)) + off
cp_idx
}
# determine Hankel matrix
h <- hmatr(ts, L=L, B=B, T=T, neig=neig)
# plot the Hankel matrix
plot(h)
```

```
# load data - N=32, cp_idx=nil, act=30 terminal, false-negative or terminal zeroes too short (3)
ts <- read.csv(file="c:/0_cerdsm/IP/gaps_freq_changepoint_detection/ts4.csv", header=TRUE,
colClasses="numeric")
ts <- as.ts(ts$ts)
len <- length(ts)
# add gaussian noise to timeseries
ts <- ts + mvrnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
cp_idx <- L + min(which(v2 > thresh)) + off
cp_idx
}
# determine Hankel matrix
h <- hmatr(ts, L=L, B=B, T=T, neig=neig)
# plot the Hankel matrix
plot(h)
```

CONTINUES IN FIG. 7C

FIG. 7B

CONTINUES FROM FIG. 7B

```
# load data - N=32, cp_idx=nil, act=29 terminal, false-negative or terminal zeroes too short (4)
ts <- read.csv(file="c:/0_cerdsm/IP/gaps_freq_changepoint_detection/ts5.csv", header=TRUE,
colClasses="numeric")
ts <- as.ts(ts$ts)
len <- length(ts)
# add gaussian noise to timeseries
ts <- ts + mvrnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

```
# load data - N=32, cp_idx=nil, act=27 terminal, false-negative or terminal zeroes too short (6)
ts <- read.csv(file="c:/0_cerdsm/IP/gaps_freq_changepoint_detection/ts6.csv", header=TRUE,
colClasses="numeric")
ts <- as.ts(ts$ts)
len <- length(ts)
# add gaussian noise to timeseries
ts <- ts + mvrnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh)) > 0){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

CONTINUES IN FIG. 7D

*FIG. 7C*

CONTINUES FROM FIG. 7C

```
# load data - N=32, cp_idx=32, act=28 terminal, del=4
ts <- read.csv(file="c:/0_cerdsm/RP/gaps_freq_changepoint_detection/ts7.csv", header=TRUE,
colClasses="numeric")
ts <- as.ts(ts$ts)
len <- length(ts)
# add gaussian noise to timeseries
ts <- ts + rnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

```
# load data - N=32, cp_idx=nil, act=none, true-negative
ts <- read.csv(file="c:/0_cerdsm/RP/gaps_freq_changepoint_detection/ts8.csv", header=TRUE,
colClasses="numeric")
ts <- as.ts(ts$ts)
len <- length(ts)
# add gaussian noise to timeseries
ts <- ts + rnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

CONTINUES IN FIG. 7E

FIG. 7D

CONTINUES FROM FIG. 7D

```
# load data - N=32, cp_idx=nil, act=none, true-negative
ts <- read.csv(file="c:/0_cerdsm/IP/gaps_freq_changepoint_detection/ts9.csv", header=TRUE,
colClasses="numeric")
ts <- as.ts(ts$ts)
len <- length(ts)
# add gaussian noise to timeseries
ts <- ts + rnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

```
# load data - N=32, cp_idx=nil, act=none, true-negative
ts <- read.csv(file="c:/0_cerdsm/IP/gaps_freq_changepoint_detection/ts10.csv", header=TRUE,
colClasses="numeric")
ts <- as.ts(ts$ts)
len <- length(ts)
# add gaussian noise to timeseries
ts <- ts + rnorm(len, 0.0, 0.01)
# set params for SSA
L <- len %/% 3
B <- len %/% 2
T <- L
neig <- L %/% 2
# perform SSA
s <- ssa(ts, kind="1d-ssa", L=L, column.projector="centering", row.projector="centering")
# calculate factor vector of Hankel matrix, row detection fn
v2 <- round(abs(calc.v(s, 2)),2)
# detect changepoint (if any) and determine index of detected changepoint
if (length(which(v2 > thresh) > 0)){
  cp_idx <- L + min(which(v2 > thresh)) + off
  cp_idx
}
# determine Hankel matrix
h <- hmatr(ts, L=L, B=B, T=T, neig=neig)
# plot the Hankel matrix
plot(h)
```

FIG. 7E

COMPUTER-DECISION SUPPORT FOR PREDICTING AND MANAGING NON-ADHERENCE TO TREATMENT

CROSS-REFERENCE TO RELATED APPLICATIONS

This application claims priority to Provisional Patent Application No. 62/437,655, filed Dec. 21, 2016, and entitled "COMPUTER-DECISION FOR PREDICTING AND MANAGING NON-ADHERENCE TO TREATMENTS," the entire contents of which is incorporated herein by reference in its entirety.

BACKGROUND

Chronic prescribed health care regimens or court-mandated programs such as probation or parole are increasingly common. In a 2010 report, the Pew Charitable Trust noted that the number of Americans under supervision by the criminal justice system has grown ten-fold since 1980. In 2006, the U.S. made up less than 5% of the world's population but had approximately 25% of the world's incarcerated population, incarcerating at rates over four times higher than the world average. The current prevalence of Americans under correctional supervision in the community is 4.7 million, either on probation or parole. Probationers and parolees are required to contact their case managers at regular intervals stipulated by the court. Failure to do so may result in revocation of parole and initiation of additional criminal justice action.

Of those who failed to violate the terms of their probation, forty percent of formal probation violations resulted in revocation of parole. The other sixty percent of formal probation violations were continued on probation with the following outcomes: 33 percent had received extended probation terms: 24 percent received jail or prison time; 22 percent had other administrative actions, such as intensified monitoring; 1 percent received new or modified conditions of probation; 15 percent had no changes made to their probation; and 5 percent of the outcomes were unknown due to missing data.

With regard to chronic health conditions, approximately half of all adults in the U.S.—more than 117 million people—have one or more chronic health conditions requiring ongoing management, preferably with the assistance of case managers and periodic scheduled visits, according to the CDC. When psychosocial issues (for example: depression, low income, or lack of social support) are present amongst individuals with chronic conditions, the impact on costs is increased. These underlying psychosocial issues can have a significant impact on how an individual adheres to ongoing therapeutic and preventive interventions for their chronic conditions. In particular, 29% of adults with a medical condition also have mental disorders. While there have been attempts to provide a technological solution, technology has largely failed to provide a reliable and accurate solution.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies are provided for the automatic identification of target subjects having a risk of relapse, non-adherence, or absconding. These persons may include individuals who are at risk for newly-incident recidivism or other non-adherence to a prescribed program, such as a program that may entail a series of actions required by the persons, visits, and/or reporting episodes. In particular, embodiments of these technologies utilize singular spectrum analysis (SSA) to analyze temporal properties of a time series determined from measured or observational data, which may be acquired by a measurement device, to determine an emergent pattern. Based on this pattern, a risk of relapse, non-adherence, or absconding over a future time interval by the individual may be determined and utilized to implement an intervening action. For example, based on the predicted risk, one or more actions may be carried out automatically or may be recommended by a decision support tool, such as, without limitation, providing notification to a caregiver or supervisor, and/or implementing changes to treatment programs or regimens, increasing observations, or changing care plans. In some embodiments, the prediction may be stored and compared against future predictions to determine whether a patient's risk has changed.

For example, aspects described herein relate to a method for developing a predictive model configured for predicting the likelihood of non-adherence for an individual. The method includes receiving information about a target subjects adherence to a prescribed program of events. The program of events may be assigned my third-party agencies and may include attending specific locations at a specific time, periodic visits, attendance and/or participation in online sessions, or the like. A timeseries of the adherence information is analyzed to determine a possibility of recidivism, non-adherence, and/or absconding for the target subject, compared to a decision threshold, and an action automatically take in the possibility of recidivism, non-adherence, and/or absconding exceeds the decision threshold. The action may include, for example, providing notification to a caregiver or supervisor, and/or implementing changes to treatment programs or regimens, increasing observations, or changing care plans. Further, the possibility of recidivism, non-adherence, and/or absconding may be compared to past results and the information provided to a caregiver, case manager, or supervisor.

Another aspect described herein relates to systems, methods, and media for receiving session log data, wherein the session log data comprises at least an indication of a target subject's performance of prescribed program events. Based on at least the session log data a timeseries of historical activity may be generated and analyzed. Analysis of the timeseries may include determining a statistical relationship between a set of input variables and an outcome of a singular spectrum analysis (SSA) computation, a Markov dynamic programming computation, a CUSUM computation. Bayesian quickest detection computation, a Lorden's test, a Page's test, a hierarchical divisive estimation computation, or a group-fused Lasso computation. Based on the analysis a possibility of recidivism, non-adherence, and/or absconding for the subject associated with the session log data is determined, compared to a decision threshold, and an action automatically take in the possibility of recidivism, non-adherence, and/or absconding exceeds the decision threshold.

In this way, some embodiments may provide a leading indicator of near-term future abnormalities, proactively notifying supervisory personnel responsible for the person and providing such personnel with timely notice to enable effective corrective, preventive, or trend-modifying maneuvers to be undertaken. Some embodiments also facilitate subject tracking, monitoring, and/or warning and learning and reinforcing systems and methods that permit prediction of non-adherence or absconding. Moreover, the embodiments are compatible for use in general care venues and afford a degree of robustness against transient or intermittent non-appearances that are low-risk, and against variations in individual conditions and logistical factors that relate to the individual's ability to adhere to the prescribed program. As such, embodiments of the technology described herein provide for a counter-conventional technological solution that is unknown in the industry and the area of clinical support.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is described in detail below with reference to the attached drawing figures, wherein:

FIGS. 4A and 4B depict SSA prediction examples including SSA interpretation, the corresponding timeseries, and heterogeneity matrix, in accordance with an embodiment of the disclosure;

FIGS. 6A-6J and 7A-7E illustratively depict examples embodiments of a computer program routine for generating a forecast predicting emergent relapse or non-adherence in an individual in accordance with an embodiment of the disclosure.

DETAILED DESCRIPTION

Figure 1A:
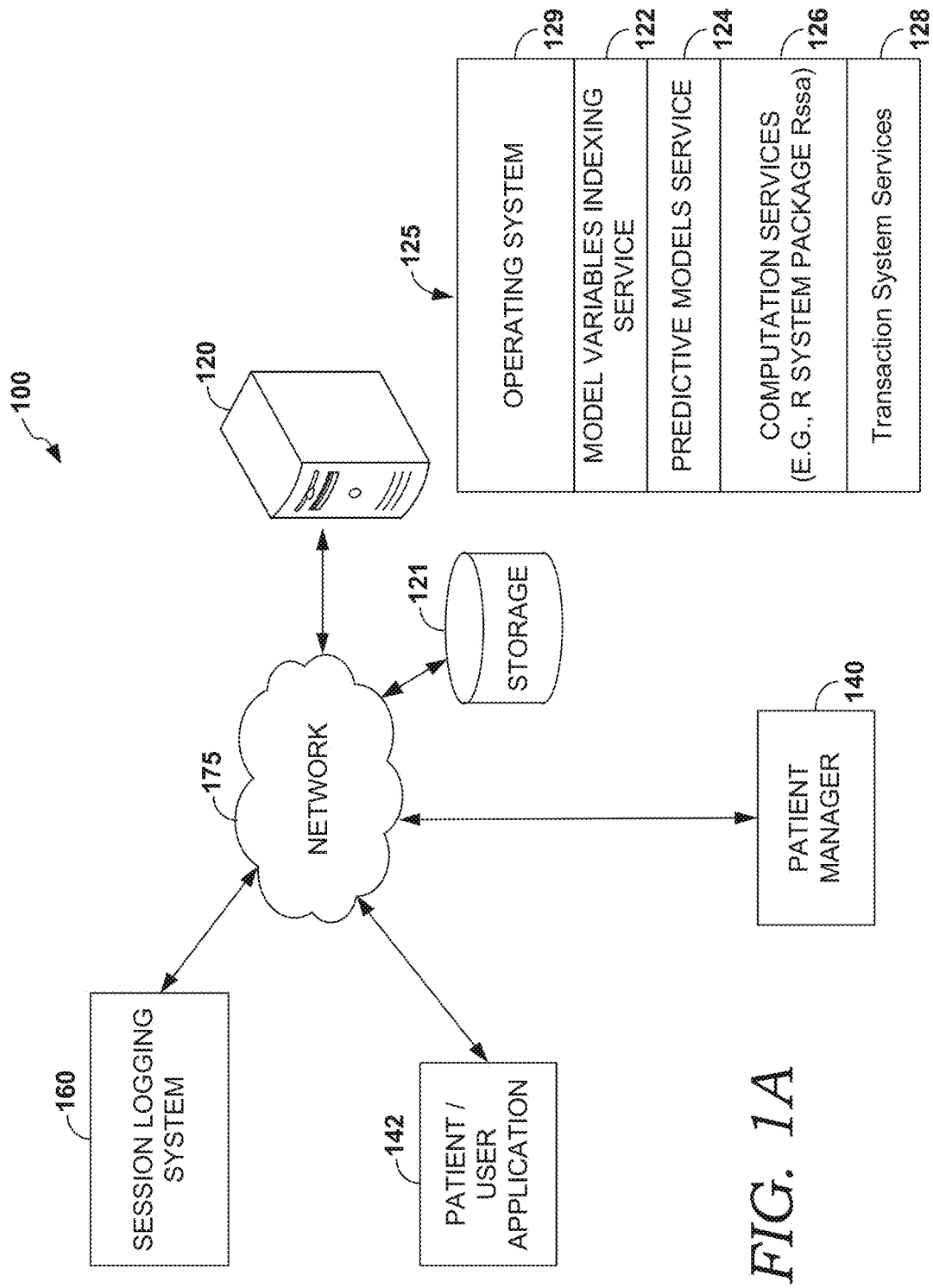
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Aspects of the technology described herein may be utilized for identifying target human individuals having a risk of relapse, non-adherence, or absconding to or from a prescribed program. Additionally, embodiments of the technology may be utilized for predicting and that risk, which may be determined as a forecast over a future time span, in some embodiments, and evaluating it to further determine or invoke specific actions to mitigate the risk or otherwise improve likelihood of compliance. As described above, these individuals may include persons who are at risk for newly-incident recidivism or non-adherence to a prescribed program, such as a program that may entail a series of actions required by the persons, visits, and/or reporting episodes (which may be referred to herein as program events or events).

But it should be noted that the focus of some embodiments is not on managing the individual person. Rather, some embodiments described herein provide improved decision support technology for identifying future instances of non-adherence. In particular, existing decision support technology utilized by case managers or caregivers to manage these prescribed program administration and patient/user compliance, is incapable of effectively determining high-risk individuals, which may (after identification) need heightened care, different procedures of program administration, or other additional support or resources. In many instances, the conventional technology utilized to manage these programs doesn't even include functionality for automatically identifying, flagging individuals at risk, or modifying, or recommending changes to the administration of their program.

Embodiments of the technologies described herein utilize singular spectrum analysis (SSA) to analyze temporal properties of a time series determined from measured or observational data relating to these events, which may be acquired by a measurement device, to determine an emergent pattern. For example, the data may pertain to logging medication usages or appearances of a person according to a prescribed health plan of care (e.g., attendance at group therapy sessions, recording of daily weights or symptoms, engagement in telehealth consultation with a case-manager, medication administration events, and similar programs); status data relating to community re-entry programs for parolees (e.g., job training, temporary housing, rehabilitation, drug testing, life coaching, and similar re-entry programs); social services data; school data, and in some embodiments demographic data, time and date data. Based on this pattern, a risk of relapse, non-adherence, or absconding over a future time interval by the individual may be determined and utilized to implement an intervening action. In some embodiments, the prediction classification, intervening action, and/or decision-support alert signal emitted are provided at logistically convenient times early in the course of incipient non-adherent behavior or absconding.

Accordingly, as will be further described herein, one embodiment comprises a method for providing a forecast predicting emergent non-adherence (e.g., relapse, absconding, or other non-adherence) in an individual, where the features are of a type as are likely to eventuate in non-adherent behaviors. For a target individual enrolled in a prescribed program, such as described herein, historical user activity is obtained for completed performance of prescribed program events over a span of time. For example, historical data values, which may be obtained automatically from a measurement device or recorded from an observer, indicating completed portions of program performances, such as, without limitation, appearances at scheduled events, self-administering treatment sessions, instances of taking medication on schedule, or adhering to behavior constraints (e.g., the user not being located at a bar, or certain locations). From the historical user activity, a logged event time series is determined. In some embodiments, the time dimension of the logged event timeseries may be transformed, for example, into logarithmically-transformed time. Additionally, some embodiments may add random noise (such as Gaussian noise) to the logged event time series.

A number of parameters are also determined or set, including one or more of a decision threshold P, offset, noise amplitude, window length L, base series length B, and neighborhood size (corresponding to a number of eigen-triples to consider for calculating projections). In some embodiments, the parameters may be pre-determined by a clinician, caregiver, or supervisor, may be based on a policy or regulation, and/or may be based on the particular prescribed program of the individual or their health condition. Next, a singular spectrum analysis (SSA), which may use column- and row-projector centering, is determined based on the parameters and the logged event timeseries, and from this a heterogeneity matrix is determined. In one embodiment, the heterogeneity matrix comprises a Hankel matrix. A matrix factor vector (such as a Hankel matrix factor vector) is then calculated using the heterogeneity matrix. The matrix factor vector is then utilized as a model forecast for emergent non-adherence or absconding.

A comparison is performed between the threshold parameter P and the matrix factor vector. If the threshold P is satisfied, then it is likely that the individual will not adhere to the program or will abscond, and an action may be implemented, such as issuing a notification or other action described herein. However, if the threshold P is not satisfied, then there is not sufficient risk for non-adherence or absconding, and in some instances prescription program resources (e.g. resources used for monitoring or compliance) may be diverted to other individuals as needed. In some embodiments, the prediction may be provided to appropriate caregivers associated with the subject and/or used for scheduling an intervention or otherwise modifying a care for the subject, such as increasing monitoring, pharmaceutical combinations, or reaching out to the subject, for example. In some embodiments, the prediction may be stored and compared against future predictions to determine whether a patient's risk has changed. In some embodiments, the prediction comprises a model forecast that may be incorporated into a decision-support tool for use by caregivers, supervisors, or managers, to facilitate managing the individual's compliance to the prescribed program and/or carrying out one or more of the actions described previously. Some embodiments integrate with other decision support tools and related tools, such as Cerner Millennium orders, Discern Expert CDS, iView, or similar applications.

Additionally, in one respect, some embodiments provide new and useful subject tracking, monitoring, warning and learning and reinforcing systems and methods that permit tracking the adherence of subjects to a prescribed program that involves periodic visits or reporting episodes, while at the same time learning, updating and promptly reporting recidivism and prohibited non-adherence of a subject.

In another respect, some embodiments provide subject tracking, monitoring, warning, and learning systems and methods that permit discovery of de facto patterns of compliance that represent pragmatic, low-risk behaviors for each subject, learning individual subject behavior patterns and dynamically adapting the statistical prediction of relapse, recidivism, or non-adherence in the context of said recent historical patterns of the subject. In yet another respect, some embodiments provide subject tracking, monitoring, warning, and learning systems and methods that make use of reinforcement learning whereby subjects may be rewarded for adherence to prescribed behavior patterns, even though the patterns contain transient, intermittent low-risk non-attendance events. In still another respect, some embodiments provide subject tracking, monitoring, warning, and learning systems and methods that permit simultaneous monitoring of a plurality of subjects from a subject control center. In some embodiments, these respects are achieved by technology for monitoring and learning a subject's behavior and logging (storing) a prescribed program's scheduled and completed visits or reporting events in a computer system.

The failure of an individual or patient to comply with a prescribed plan-of-care for a health condition, or non-achievement of rewards and incentives in preventive programs (i.e. other types of prescribed programs), involves recidivistic non-adherence or absconding by the patient. In some ways, this is analogous to parole and probation violations and bail-jumping.

Many of these prescribed programs involve engagement with case managers via online telehealth apps or phone calls or web-based logs or require serial appearances at clinic locations for check-ups or exams. Absconding, passivity or failure to participate, failing to maintain attendance at work or school, failing to keep up-to-date and pay restitution or co-pays or other fees on-time are relevant examples of recidivism in health services, all of which result in "gaps" or discontinuities of care, which can jeopardize achieving the intended outcomes. Similar situations also arise in other fields where longitudinal persistence is fundamental to a program's or services' efficacy, such as addiction management, programs for the homeless, and programs of religious institutions. One needs to identify quickly those who are likely disengaging from the program and respond promptly with intensified contact or other interventions.

Technology for identifying emergent relapse or non-adherence also may be utilized in sales and marketing campaigns for products and services that are purchased on a chronic, ongoing basis and where consumer switching to a competitor's brand justifies "we want you back" promotional offers. For instance, such offers are usually effective only if tendered quickly, prior to the expiry of a competitor's trial period and prior to the time when the consumer will have entered into a contract with the competitor.

Moreover, there is an increasing interest in longitudinal monitoring systems and methods for monitoring target subjects, such as prisoners or parolees, or persons participating in a court-ordered rehabilitation program for addiction behaviors, or persons receiving a prescribed plan of care for chronic health condition, such as diabetes or heart failure or chronic obstructive lung disease or cancer or HIV. Various technologies have been developed for determining whether or not a target subject is presently located a specified location, such as at his house, or whether or not a person enrolled in a prescribed health services plan-of-care is presently adhering to the series of check-up visits that are scheduled. But these technologies are not capable of providing a prediction of future likelihood (or risk) of non-adherence.

The manner in which jurisdictions respond to violations of parole or probation or health care plans-of-care (VOPs) should be thoughtful and deliberate. Although each case requires individual decision making, the response to a given violation should be consistent with policy developed by that jurisdiction. Agency non-adherence and violation policies should governed by such considerations as assessment of risk posed by the target subject, case-processing requirements, local resources availability, and the outcomes desired by the Agency for certain types of non-adherence or violations. Improved Agency recidivism and VOP detection tools are needed, to guide staff in making supervisory decisions, to conserve staff time and resources, and to assist decision makers in reaching consistent and equitable dispositions. If possible, such tools should help to match responses to the severity of violation behavior and hold offenders accountable for their behavior. Policymakers must understand the type of offenders in their system as well as the capacity and purposes of the existing range of options available to respond to offenders' violation behavior.

In some of the embodiments described herein, low-risk subjects who have non-serious, intermittent non-appearance VOP events are identified and are distinguished from high-risk subjects whose patterns of non-appearances are strongly associated with deliberate, recidivistic non-adherence or absconding. In this way, the technologies provided by these embodiments are advantageous as they enable case managers to promptly detect emergent, serious relapse or non-adherence in real time. These embodiments are further advantageous in that they enable case managers to predict and prevent or correct recidivism.

In some instances, field Monitoring Devices (FMDs) may be used to record information concerning the presence or attendance of the target subject at the sanctioned locations. This information may be transmitted to a computer system in a centralized monitoring center. Various forms of electronic monitoring technology and radio frequency identification tags may be utilized for identifying target subjects and monitoring their present general status or behavior. Voice verification methods may be utilized for identifying particular target subjects to insure their presence at specified location. Secured straps and tamper-indicating fastening mechanisms that generate alarms if removal is attempted may be utilized for attaching tags or other identification mechanisms to target subjects. Similar voice verification and online login credentials may be used in health services apps, to confirm participation in and completion of prescribed learning content by target subjects having chronic health conditions.

In some instances, "no-show" occurrences are due to the subject's inability to obtain transportation to the location of the scheduled visit. In other instances, constraints associated with employment or child-care or other logistical issues are the reason for the non-appearance at the designated visit. Such occurrences are often transient or one-time events and, as such, do not represent serious non-adherent or violative behavior or change of intention on the part of the target subject. Intermittent, mildly non-adherent occurrences should not cause supervisory personnel to expend large amounts of time and resources to address a non-existent problem. However, persistent VOP non-adherence may reflect a change of intention and a deliberate refusal to comply. To be effective in addressing the interests of the community and of the individual, detection of relapse or non-adherence should be accomplished as quickly as possible once non-adherent behavior commences, so that appropriate corrective action can be undertaken.

Conventional approaches to addressing the problems solved by the embodiments provided herein often entail waiting until a specific time interval has elapsed or until a specific number of visits has been missed or a specific number of VOPs has been logged. This may appear to have the advantage of simplicity. However, it is a severely "lagging" indicator and is associated with delays of detection and corrective action that are longer than optimal. Furthermore, it fails to take into account the context-sensitive, idiosyncratic patterns of intermittent or transient occurrences that do not reflect true non-adherence (which are taken into account in some of the embodiments provided herein, and which provide advantages as further described herein). Consequently, these conventional approaches tend to produce excessive "false-positive" signals, leading to overly aggressive, intrusive pursuit of subjects whose intentions to adhere have not in fact altered. The repeated intrusions tend to inadvertently impugn the character of the subject and compound their feelings of guilt about their intermittent non-attendance. The intrusions infantilize the subject and give rise to adversarial attitudes about the surveillance policies of the supervisor or case manager.

Some of the reasons why people interrupt their adherence include the perception that their condition is a common problem, fear or uncertainty as to what the case manager will do at the time(s) of the visit(s), misapprehensions about prejudices held by case managers of different racial or ethnic group than the subject, optimism that the condition would go away of its own accord, doubt that the supervisor would pursue non-adherent behavior, lack of knowledge, and difficulty in accessing the services-such as getting appointments with the case manager; difficulty getting transportation to the location for the schedule visit; difficulty getting off work to attend the scheduled visits.

In a health care context, "no-shows" are often associated with significant excess costs in health care. "No-shows" and gaps in care continuity are associated with inferior outcomes for mental health conditions, diabetes, cancer, and other chronic health conditions. It is also known that the care plan non-adherence ("no-shows" and "failure to schedule appointment") rate is sensitive to rurality, age, gender, severity of health condition, and other attributes. Limitations of conventional approaches include failure to account for occasional or intermittent low-risk "no-show" occurrences that do not reflect any change in the target subject's intention to adhere with the prescribed program.

Embodiments described herein address these and other limitations of the conventional technology by providing improved decision-support technology including predictive functionality, and in particular for some embodiments, providing prediction classification, intervening action (or recommended actions), and/or decision-support alert signals or other notification at logistically convenient times early in the course of incipient non-adherent behavior or absconding. Additional improvements or benefits include remediation of failures to comply with ordered recurring visits, improvements in achieving favorable outcomes that are in the individual's and society's interests, and reduction in consumption of resources in pursuit and follow-up with target subjects.

With regard to the latter, each local Agency spends considerable money tracking and monitoring target subjects under supervised care in their catchment areas. After a target subject is enrolled in a program (e.g., approved for release from incarceration on probation/parole; prescribed a chronic plan of health care), s/he is subject to ongoing supervision. Usually, the target subject registers with a local authority and he is assigned a case manager with whom he checks in periodically. A case manager is usually charged with one hundred or more subjects and s/he makes time to monitor and track each subject. The subject may be required to physically report to the case manager personally on a periodic basis.

Each local Agency must provide enough case managers for a given population of subjects to handle in meetings with the subjects, whether in office or by telephone or online or in the field. Most of the time, these reporting meetings are routine and no issues result from these meetings. Even though these meetings are routine and without any important issue to be resolved, the subjects still need to report at the frequency that is mandated. This reporting system is an obstacle for subjects who have jobs or who have unreliable access to and/or no access to transportation. The subject must take time off work and arrange for travel to the case manager's office for a short appointment.

The case manager, on the other hand, must make himself/ herself available under his supervision. If either the case manager or the subject is running late, it puts the rest of the case manager's appointments behind schedule, forcing appointments to be rescheduled, and the subject may be less able to comply with a rescheduled appointment than with the appointment as originally scheduled. Notably, case managers' subject caseloads have recently grown dramatically without corresponding growth in resources to help manage the larger case load. Case managers now have to determine which subjects are at greatest risk of recidivism requiring immediate intervention and which subjects represent a lesser risk not requiring intervention. The challenge for case managers is determining and prioritizing which subjects are at greatest risk of recidivism requiring the most of amount of intervention. If every instance of non-attendance caused revocation (of prescribed health plan-of-care, probation, parole, etc.), there would not be enough resources available to handle the load.

In this setting, much time and resources are wasted by case managers attending to low-risk subjects instead of attending to those subjects at greatest risk of recidivism. Further, the setting described above follows a reactive regime, wherein the case manager monitors a subject and reacts to what the subject does or does not do, after the fact. Previously, a case manager would not have information to anticipate what may likely happen to the subject. Thus, the case manager cannot act proactively to guide the subject or prevent recidivism.

Accordingly, yet another advantage of these embodiments, which may be implemented as decision support technology utilized by a monitoring and management system, is that providing decision support based on a "recidivism prevention model" enable case managers to handle a larger case load by anticipating which subjects are at greatest risk to recidivate and it is this system that the present invention is primarily directed to. In particular, the embodiments disclosed herein enable timely detection of those who are non-adherent/absconding. For example, one predictive embodiment identifies those in whom intensified monitoring will be needed.

While attempts have been made to provide a technological solution to improve decision support systems so as to overcome these deficiencies, conventional technology has largely failed to provide a reliable and accurate solution. For example, conventional technological systems developed to address these, and other limitations, have failed to remove human bias, like case manager bias, created by a cumulative reactionary response. The overly aggressive, intrusive, and/ or delayed responses fostered by conventional technological systems can undermine the subject's capacity to complete a program. Further, conventional technological attempts fail to intervene and instead allow failure to occur and at most report the failure. Notably, these problems and the other failures of previously attempted solutions discussed herein cannot be overcome by simply using a computer. This is because, at least in part, solving the problems with the conventional technology require new and improved techniques that specifically overcome these drawbacks. Hence, the embodiments discussed herein overcome these disadvantages by implementing new and improved techniques and features that are not know in conventional industry practice, and thereby providing enhanced decision support systems that are capable producing reliable and accurate determinations that have not been previously achieved.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R. or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes a session logging system 160, which may be part of one or more electronic health record (EHR) systems, communicatively coupled to network 175, which is communicatively coupled to computer system 120. In some embodiments, components of environment 100 that are shown as distinct components may be embodied as part of or within other components of environment 100. For example, session logging system 160 may comprise one or a plurality of record/logging systems such as sensor/monitor logging systems, hospital EHR systems, health information exchange EHR systems, clinical genetics/genomics systems, ambulatory clinic EHR systems, psychiatry/neurology EHR systems, insurance, collections or claims records systems: and may be implemented in computer system 120. In an embodiment, session logging system 160 includes historical data for patient addition treatment, relapse information, other health services, claims data, apportionment data, and/or related health services financial data.

In some embodiments, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet. and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of session logging system 160 may comprise one or more data stores of health records, which may be stored on storage 121, and may further include one or more computers or servers that facilitate the storing and retrieval of the health records. In some embodiments, session logging system 160 may be implemented as a cloud-based platform or may be distributed across multiple physical locations. Session logging system 160 may further include record systems, which store real-time or near real-time patient (or user) information, such as wearable, bedside, or in-home patient monitors or sensors, for example. Although FIG. 1A depicts an exemplary session logging system 160, it is contemplated that an embodiment relies on patient manager 140 and/or patient/user application 142 for accessing, storing and/or retrieving patient record information.

Example operating environment 100 further includes a patient/user application 142 communicatively coupled through network 175 to treatment/relapse logging system 160. Although environment 100 depicts an indirect communicative coupling between application 142 and treatment/relapse logging system 160 through network 175, it is contemplated that an embodiment of application 142 is communicatively coupled to treatment/relapse logging system 160 directly. An embodiment of application 142 comprises a software application or set of applications residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the disclosure, which may be used by the target user at risk for non-adherence (e.g., relapse, absconding, or other non-adherence), a social worker, a supervisor, manager, or caregiver associated with the target user. For example, in one embodiment, application 142 facilitates receiving and logging session or program event information about the target user and/or processing, interpreting, accessing, storing, retrieving, and communicating information associated with session logged records or other healthcare related records of the target user. In an embodiment, application 142 sends an alarm indication directly to patient manager 140 through network 175.

Example operating environment 100 also includes a patient manager 140 communicatively coupled through network 175 to treatment/relapse logging system 160 and patient/user application 142. In one embodiment of manager 140 comprises a user interface that may be used to facilitate access by a manager-user (including a clinician/caregiver such as a medical or psychiatric caregiver, a supervisor, employer, parole officer, etc.) to the target patient/user's health records (including information logged in component 160), and one or more prediction models for predicting likelihood of non-adherence of the target patient/user. One embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, manager 140 includes a Web-based application (which may take the form of an applet or app) or set of applications usable to manage user services provided by an embodiment of the disclosure.

In some embodiments, manager 140 facilitates accessing and receiving information from a health record, or health care provider about a specific patient, set of patients, or provider clinicians, according to the embodiments presented herein. Embodiments of manager 140 also may facilitate accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, manager 140 also facilitates receiving orders for the patient/target user from the clinician/caregiver/manager, based on the results of monitoring and/or predictions. Manager 140 may also be used for providing diagnostic services or evaluation of the performance of various embodiments.

Example operating environment 100 may further include computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on application 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, application 142 and/or manager 140 operate in conjunction with software stack 125.

In embodiments, model variables indexing (or mapping) service 122 facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124 comprises the services or routines for forecasting likelihood of patient non-adherence, which may be developed and implemented according to the method described in connection to FIG. 2.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including, in an embodiment. Rssa package, which may be utilized for singular spectrum analysis, used in the implementation of the predictive model(s) for determining likelihood of non-adherence.

In some embodiments, computational services include natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIGS. 6A-6J and 7A-7E. In some embodiments, computation services 126 use session logging system 160. Some embodiments of computation services 126 may use transaction systems services 128. Transaction system services 128 include services for facilitating transactions by a target user (such as completing or not completing prescribed program events), which may be facilitated using application 142, and/or by a clinician, caregiver, or provider, which may be facilitated using patient manager 140.

Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data: variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with treatment/relapse logging system 160. Further, although depicted as a single storage data store, data store 121 may comprise one or more data stores, or may be in the cloud.

Figure 1B:
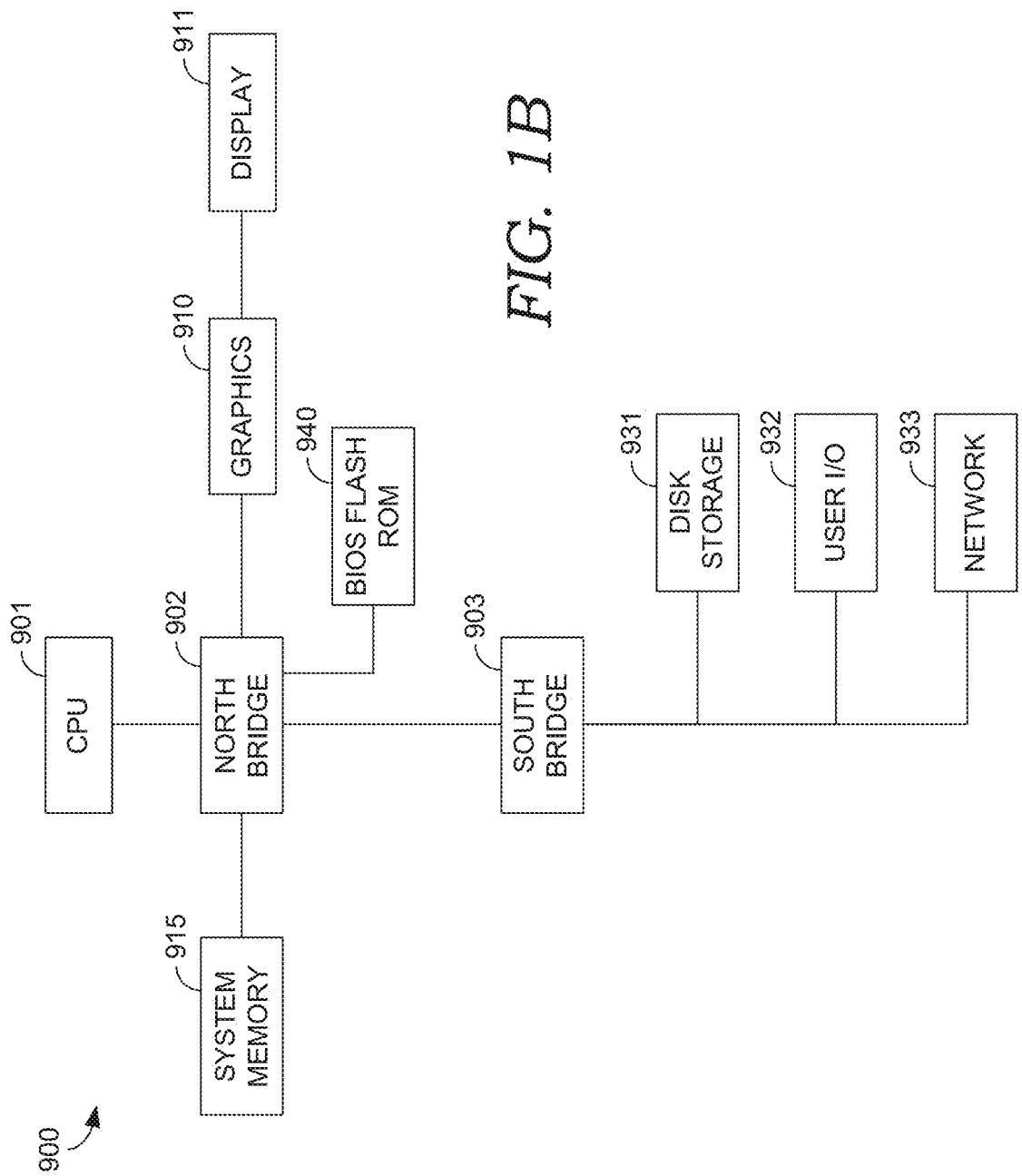

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system. While embodiments may be employed using these computing systems, various aspects of this application focus on the logical structures programmed into the computing system, since the logical structures that are carried out by the computer—not merely the computer components themselves—that realize some of the improvement over the drawbacks of the conventional industry practice.

Figure 2A:
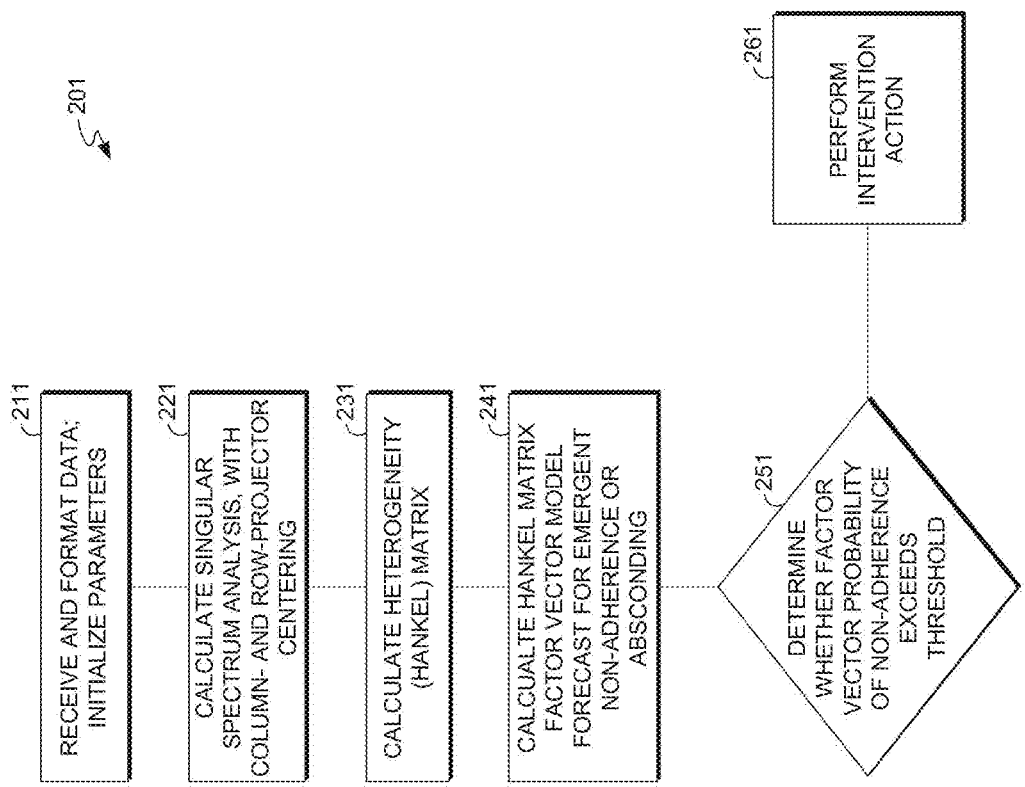
FIGS. 2A and 2B depicts a flow diagram of a method for generating a forecast predicting emergent relapse or non-adherence in an individual, in accordance with an embodiment of the disclosure.
Figure 2B:
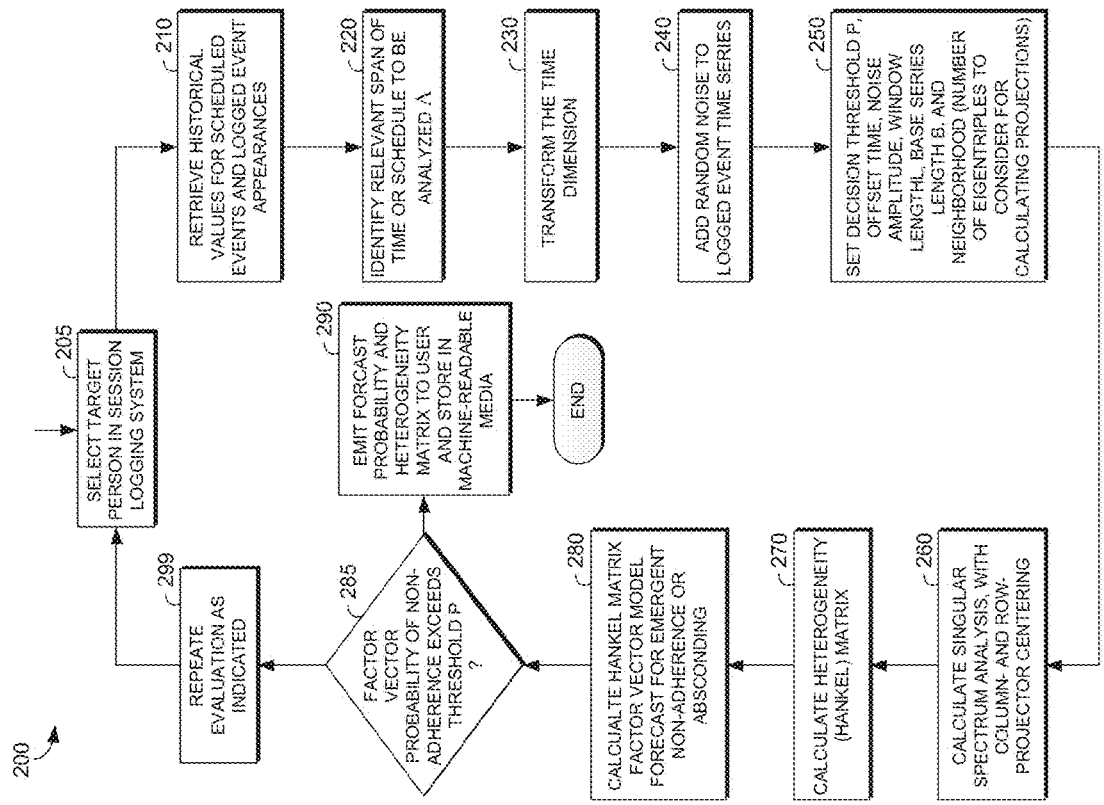

Turning now to FIGS. 2A and 2B, methods 200 and 201 are provided for determining a forecast predicting emergent relapse or non-adherence in an individual, where the features are of a type as are likely to eventuate in non-adherent behaviors. Some embodiments of the steps of method 200 and 201 are carried out using one or more computer program routines, such as the routine illustratively provided in FIGS. 6A-6J and 7A-7E. With continued reference to FIGS. 2A and 2B, some embodiments are described which may be incorporated into a computer-performed decision support tool (which may be part of a monitoring and management system) based on a "recidivism prevention model" which thereby enables patient case managers to handle a larger case load by anticipating which subjects are at greatest risk to recidivate and further enables timely detection of those who are non-adherent/absconding. However, it will be understood by those skilled in the art that this is merely a single illustrative application of the embodiments described herein and is not intended to limit the scope of the embodiments described herein.

"Change-point" analysis is the process of detecting distributional changes within time-ordered observations, such as the logged timeseries of such visits or prescribed program events. A 'change-point' is defined as the moment when a change has occurred, involving transition to a level or a process or a regime different from the one that prevailed prior to the shift or change-point. A change-point may entail a shift in level or location or a shift in dispersion or scale.

Statistical change-point processes may involve analysis of the data in the time domain. These processes also may involve measurements on interval scale, producing floating-point values. However, in some instances, and in particular in solving the problems addressed by the embodiments disclosed herein, the measurements may be categoricalbinomial or multinomial or ordinal values. In particular, adherence to a prescribed plan of medical care, or non-recidivism of offenders in criminal justice supervision programs such as parole or probation, or continued participation in a club or society are examples of such use-cases.

"Singular spectrum analysis" (SSA) is a relatively recent technique of time series analysis that employs frequency domain transformations. SSA is based on a singular value decomposition (SVD) of a 'trajectory matrix' obtained from the original time series with subsequent reconstruction of the series.

An overview of change-point detection in timeseries based on sequential application of the singular spectrum analysis is provided. A basis for the SSA process utilized in method 200 is that if at a certain time tau the mechanism generating the time series $x_t$ has changed, then an increase in the distance between the L-dimensional hyperplane spanned by the eigenvectors of the lag-covariance matrix, and the M-lagged vectors $(x_{\tau+1}, \ldots, x_{\tau+M})$ is to be expected. In some embodiments this method can be considered as a statistical procedure with the moving sum of weighted squares of random variables being the detection statistic. SSA expansion tends to pick up the main structure of the time series, if there is one. For example, this may happen when the 1-dimensional subspace of the time series approximates the M-dimensional vectors $X_1, \ldots, X_K$. If this structure is found and there are no structural changes, then the SSA continuation of the time series tends to agree with the continued original time series.

Accordingly, method 201 may being at step 211, wherein information associated with a target user or patient is received, formatted, and parameters are initialized. Some embodiments of step 211 include identifying a target user or patient with an existing record of session logging information (i.e. a record of logged prescribed program events). The target user or patient's record may be stored for example in a session logging system, such as session logging system 160. Further, step 211 may receive, access, and/or otherwise obtain historical user activity from the existing record of session logging information. For example, the target user or patient record may include records held by (or associated with) a health service provider, law enforcement agency, school, social service agency, religious service organization, a club, and/or a society. The records generally include historical data values, which may be obtained automatically from a measurement device (e.g., a Bluetooth-enabled digital inhaler device, or the like): digitized forms-completion: mobile device app events: voice, video, or other multi-media data; and/or recorded from an observer. The historical data values indicate program events, which may indicate completed portions of program performances, such as, without limitation, scheduled events or logged event appearances, self-administering treatment sessions, instances of taking medication on schedule, or adhering to behavior constraints. For example, the record(s) may be associated with past health records, criminal records, employment status, school enrollment, housing status, participation status in health coaching, training or rehabilitation programs, and substance use. In other words, a target user or patient with an existing treatment program (e.g., in-person appearances: telephonic interviews: prescribed medication dosing schedules; and so on) with at least some indication of completed portions of the program may be identified.

Figure 5A:
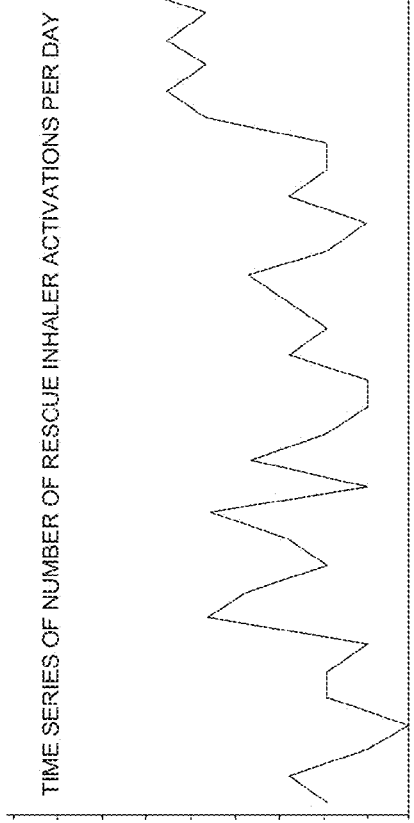
FIGS. 5A and 5B depicts aspects of an example embodiment actually reduced to practice for management of severe asthma, in accordance with an embodiment of the disclosure.

Additionally, step 211 may format the historical data by identifying a relevant span of time A or schedule from the historical data. The particular span of time may correspond to the particular prescribed program of the target user and/or a condition associated with the user, and may also be determined based on a policy of the manager's or supervisor's institution. For example, a previous time span of 1 week, month, or several months may be identified from the historical data values within the existing record for the target user or patient. Thereby determining a logged event timeseries from the target user or patient's existing record. FIG. 5A depicts an exemplary graph of the timeseries determined from an existing record of logged events. In some embodiments, the timeseries has a time dimension that is: (a) continuous actual date-time; (b) coarsened continuous date-time [for example, collapsing actual date-time to date or to week or to month]: (c) transformed continuous time [for example, logarithmically-transformed time]: or (d) discrete serial occurrences indexed in the sequence in which they occurred, regardless of the time interval that elapsed between adjacent entries in the series. In some embodiments, the timeseries includes values that are binomial, multinomial, or ordinal levels where at least one value denotes non-adherence, absconding, relapse, or recidivism.

In some embodiments of step 211, formatting the historical data may further include, transformation of the time dimension of the logged event timeseries. For example, the timeseries may be transformed into a logarithmically-transformed timeseries. In some embodiments, transformation of the time dimension of the logged event timeseries is, at least partially, facilitated by a software stack, such as software stack 125. Additionally. and/or alternatively, formatting the historical data may include, the addition of random noise to the logged event timeseries. For example, Gaussian noise may be added to the logged event timeseries. In some embodiments, the addition of random noise to the logged event timeseries is, at least partially, facilitated by a software stack, such as software stack 125.

Additionally, step 211 may initialize parameters by determining: a decision threshold P; an offset: a noise amplitude; a window length L; a base series length B; and/or a neighborhood size. Generally, these parameters may be used as inputs for SSA and/or a heterogeneity matrix. In some embodiments, the parameters may be pre-determined by a clinician, caregiver, or supervisor, may be based on a policy or regulation, and/or may be based on the particular prescribed program of the individual or their health condition. The threshold P is generally a measure of risk tolerance. It may be pre-determined by a clinician, caregiver, or supervisor, may be based on a policy or regulation, and/or may be based on the particular prescribed program of the individual or their health condition. The offset is generally used as an input to distinguish true emergent recidivism or non-adherence or absconding from one-time or transient non-attendance. In an embodiment, the offset is applied to the raw event time (or transformed-time, or visit-index). The noise amplitude may modify the amplitude of the random noise added to the timeseries. The window length L may be a fraction of the length of the timeseries A. In some embodiments, the window length L is between 0.2*Λ and 0.5*Λ, between 0.1*Λ and 0.9*Λ, and/or between $X_1$*Λ and $Y_1$*Λ where $X_1>0$ and $Y_1<1$. The base series length B may also be a fraction of the length of the timeseries A. In some embodiments, base series length B is between 0.2*Λ and 0.5*Λ, between 0.1*Λ and 0.9*Λ, and/or between $X_2$*Λ and $Y_2$*Λ where $X_2>0$ and $Y_2<1$. The neighborhood size may correspond to a number of eigentriples to consider for calculating projections. For example, the neighborhood size may be a fraction of the window length L between 0.1*L and 0.9*L, between 0.2*L and 0.5*L. and/or $X_3$*L and Y;*L where $X_3>0$ and $Y_3<1$.

Some embodiments of the step 211 are carried out using one or more computer program routines, such as the routine illustratively provided in FIGS. 6A-6J and 7A-7E. For example, code 602 and 702 depict an exemplary portion of code for receiving accessing, and/or otherwise obtaining historical user activity from the existing record of session logging information. Additionally, code 603 and 703 depict an exemplary portion of code for adding random noise (in this case Gaussian noise) to the timeseries obtained by code 602 and 702 respectively. Further, code 601 (and 701) and 604 (and 704) depict an exemplary portion of code for initializing parameters for SSA and/or heterogeneity matrix analysis. As will be understood by those skilled in the art, the routine illustratively provided in FIGS. 6A-6J and 7A-7E is intended as an example; and, as such is not intended to limit the scope of the embodiments described herein.

At step 221, a singular spectrum analysis (SSA) is determined based on a set of parameters and the logged event timeseries. In an embodiment, the SSA may use column- and row-projector centering as described above. Step 221 may additionally or alternatively rely on Markov dynamic programming computation, a CUSUM computation, or Bayesian quickest detection computation, a Lorden's test, a Page's test, a hierarchical divisive estimation computation, or a group-fused Lasso computation. Further, some embodiments of step 221 are facilitated by the parameters and the logged event timeseries from step 211. The SSA may utilize the Rssa package of the R-System, as described in connection to FIG. 1A and shown in the example computer program routines illustratively provided in FIGS. 6A-6J and 7A-7E. For example, code 605 and 705 depict SSA analysis based on the parameters and the timeseries identified.

At step 231, a heterogeneity matrix is determined. In one embodiment, the heterogeneity matrix comprises a Hankel matrix. Some embodiments of the step 231 are carried out using one or more computer program routines, such as the routine illustratively provided in FIGS. 6A-6J and 7A-7E. For example, code 608 and 708 depict Hankel matrix determination from the timeseries.

At step 241, a matrix factor vector (such as a Hankel matrix factor vector) is calculated using the heterogeneity matrix. The matrix factor vector is then utilized as a model forecast for emergent non-adherence. Examples of heterogeneity matrices and corresponding time-series are illustratively provided in FIGS. 4A and 4B. In particular, with reference to FIGS. 4A and 4B, a number of SSA prediction examples are illustratively shown, including a timeseries of logged events, a corresponding heterogeneity matrix, and an SSA interpretation. Further, some embodiments of the step 241 are carried out using one or more computer program routines, such as the routine illustratively provided in FIGS. 6A-6J and 7A-7E. For example, code 606 and 706 depict calculation of a Hankel matric factor vector.

At step 251, a comparison is performed between the threshold parameter P and the matrix factor vector. Some embodiments of the step 251 are carried out using one or more computer program routines, such as the routine illustratively provided in FIGS. 6A-6J and 7A-7E. For example, code 607 and 707 depict determination of whether factor vector probability of non-adherence exceeds the threshold parameter P. If the threshold P is satisfied, then it is likely that the individual will not adhere to the program or will abscond, and method 201 proceeds to step 261. At step 261, an action may be invoked, such as issuing a notification or other action by the decision support tool, as described herein. As a non-limiting example, some embodiments of step 261 may notify the responsible care provider (via patient/user application 142 and/or patient manager 140) of the predicted non-adherence and/or abscondance; placing new order(s) in the individual's record (such as records stored in session logging system 160); altering the individual's prescribed program events; reserving resources, for the individual, in a care facility needed to treat and/or manage the consequences of potential non-adherence; ordering increased monitoring of the individual; ordering increased testing of the individual: and/or ordering prescriptions for the patient; issuing an electronic alert or notification to a responsible manager and/or the individual.

Turning now to FIG. 2B and method 200, another exemplary method is provided for determining a forecast predicting emergent relapse or non-adherence in an individual, where the features are of a type as are likely to eventuate in non-adherent behaviors. Accordingly, method 200 begins at step 205, wherein a target user or patient is identified for which a record of session logging information (i.e. a record of logged prescribed program events) exists. In this embodiment of method 200, the target user (or patient) will be evaluated to determine a likelihood of future non-adherence to a prescribed program. Some embodiments of method 200 may run in parallel or sequentially across multiple individual patients in a particular program. At step 210, historical user activity is obtained for the target user for completed performance of prescribed program events. The records generally include historical data values, which may be obtained automatically from a measurement device (e.g., a Bluetooth-enabled digital inhaler device, or the like); digitized forms-completion; mobile device app events; voice, video, or other multi-media data and/or recorded from an observer. The historical data values indicate program events, which may indicate completed portions of program performances, such as, without limitation, scheduled events or logged event appearances, self-administering treatment sessions, instances of taking medication on schedule, or adhering to behavior constraints. For example, the record(s) may be associated with past health records, criminal records, employment status, school enrollment, housing status, participation status in health coaching, training or rehabilitation programs, and substance use. In other words, a target user or patient with an existing treatment program (e.g., in-person appearances; telephonic interviews: prescribed medication dosing schedules; and so on) with at least some indication of completed portions of the program may be identified.

At step 220, a relevant span of time A or schedule to be analyzed is identified. For example, a previous time span of 1 week, month, or several months, may be determined in step 220. The particular span of time may correspond to the particular prescribed program of the target user and/or a condition associated with the user, and may also be determined based on a policy of the manager's or supervisor's institution. Some embodiments of step 220 (or step 220 in combination with step 210) determine a timeseries of the historical activity retrieved in step 210 for the span of time (or schedule) identified in step 220. Thus from the historical user activity, a logged event timeseries is determined.

At step 230, in some embodiments, the time dimension of the logged event timeseries may be transformed, for example, into logarithmically-transformed time, and at step 240, in some embodiments, random noise (such as Gaussian noise) may be added to the logged event timeseries.

At step 250, one or more parameters are determined including a decision threshold P, offset, noise amplitude, window length L, base series length B. and/or neighborhood size (corresponding to a number of eigentriples to consider for calculating projections). In some embodiments, the parameters may be pre-determined by a clinician, caregiver, or supervisor, may be based on a policy or regulation, and/or may be based on the particular prescribed program of the individual or their health condition. At step 260, a singular spectrum analysis (SSA), such as described above and which may use column- and row-projector centering, is determined based on the parameters and the logged event timeseries. Some embodiments of step 260 utilize the Rssa package of the R-System, as described in connection to FIG. 1A and shown in the example computer program routines illustratively provided in FIGS. 6A-6J and 7A-7E.

At step 270, a heterogeneity matrix is determined. In one embodiment, the heterogeneity matrix comprises a Hankel matrix. At step 280, a matrix factor vector (such as a Hankel matrix factor vector) is then calculated using the heterogeneity matrix. The matrix factor vector is then utilized as a model forecast for emergent non-adherence. Examples of heterogeneity matrices and corresponding time-series are illustratively provided in FIGS. 4A and 4B. In particular, with reference to FIGS. 4A and 4B, a number of SSA prediction examples are illustratively shown, including a timeseries of logged events, a corresponding heterogeneity matrix, and an SSA interpretation.

Returning to FIG. 2B, at step 285 of method 200, a comparison is performed between the threshold parameter P and the matrix factor vector. If the threshold P is satisfied, then it is likely that the individual will not adhere to the program or will abscond, and method 200 proceeds to step 290. At step, 290, an action may be invoked, such as issuing a notification or other action by the decision support tool, as described herein. As a non-limiting example, some embodiments of step 290 may notify the responsible care provider (via patient/user application 142 and/or patient manager 140) of the predicted non-adherence and/or abscondance; placing new order(s) in the individual's record (such as records stored in session logging system 160); altering the individual's care plan; reserving resources, for the individual, in a care facility needed to treat and/or manage the consequences of potential non-adherence; ordering increased monitoring of the individual: ordering increased testing of the individual; and/or ordering prescriptions for the patient; issuing an electronic alert or notification to a responsible manager and/or the individual.

However, if the threshold P is not satisfied, then there is not sufficient risk for non-adherence or absconding, and method 200 proceeds to step 299, where method 200 may be repeated as needed. In some instances, where the threshold P is not satisfied, prescription program resources (e.g. resources used for monitoring or compliance) may be diverted to other individuals as needed. Additionally, some embodiments of method 200 provide the model forecast prediction to appropriate caregivers associated with the subject, for scheduling an intervention, or otherwise modifying a care for the subject, such as increasing monitoring, pharmaceutical combinations, or reaching out to the subject, for example. In some embodiments, the model forecast may be stored and compared against future predictions to determine whether a particular patient's risk has changed.

EXAMPLE REDUCTIONS TO PRACTICE

With reference now to FIGS. 5A-7E and continuing reference to FIGS. 2A, 2B, and 4A-4B, two example embodiments reduced to practice are now described. These example embodiments comprise a system and method for time series properties-based early detection of emergent recidivism or non-adherence. These example embodiments were implemented in part using the computer program routines illustratively provided in FIGS. 6A-6J and 7A-7E.

Example #1—Missed Appointments

Large observational electronic health record (EHR) derived de-identified datasets such as Cerner Health Facts® data warehouse were utilized to (a) to discover patterns that denote incipient relapse or non-adherence and (b) to develop predictive mathematical models that identify who will benefit from adherence-promoting interventions and who will not. Records were retrieved from a patient health records data warehouse, which is derived from Cerner electronic health records (EHR) from 100% of episodes of care that are incident upon the participating health institutions. The personally-identifiable information was removed in conformance with U.S. HIPAA law and regulations, and the de-identified data were stored in a separate, secure database. A total of 103 ambulatory patients' records contained 32 or more date-time stamped values for each of a variety of laboratory and physiologic parameters that were contemporaneous with the doctor's office or outpatient clinic episodes. The as-treated dataset contained measurements of the parameters as arose in the course of conventional visit scheduling practices in an ambulatory clinic setting. It should be noted that these temporal patterns are of such complexity and variability that it would be beyond the capability of a human being to examine the occurrences of records denoting the patient's appearance or not at scheduled outpatient visits and to determine conformity or not to the prescribed plan of care.

Figures 3A, 3B:
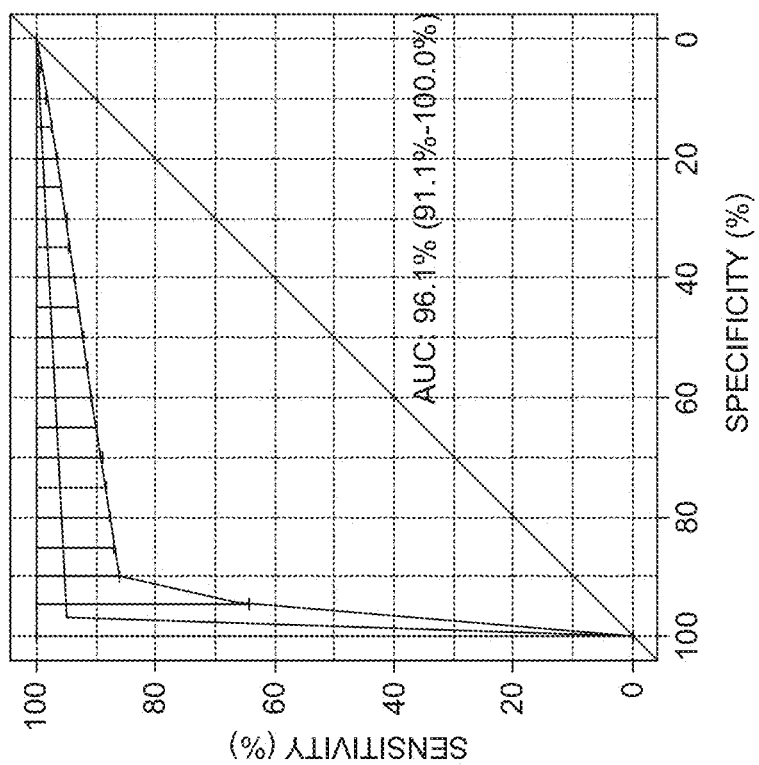
FIGS. 3A and 3B depict aspects of an example embodiment actually reduced to practice for predicting risk for non-adherence, including a receiver operating characteristic (ROC) curve and statistical performance of the example embodiment.

Using the foregoing variables, the Rssa package means of the R system was used to construct SSA change-point detection models for the association of the input biomarker variables with emergence of non-adherence to the prescribed plan of care. As depicted in FIG. 3A, the region of convergence (ROC) area under the curve in the final composite model for this time series data set for this example embodiment reduced to practice was 0.%.

Example #2—Non-Adherence to Asthma Plan-of-Care

Asthma is characterized by chronic inflammation of the airways and recurrent exacerbations with wheezing, chest tightness and cough. Treatment with inhaled steroids and bronchodilators often results in good control of symptoms, prevention of further morbidity and mortality, and improved quality of life. Management of moderate to severe asthma frequently entails use of long-acting beta-agonist (LABA) medications, inhaled corticosteroids, leukotriene inhibitor medications, omalizumab or other medications that inhibit the binding of IgE immunoglobulin to FcεRI receptors on the surface of mast cells and basophils, tiotropium or other long-acting antimuscarinic agents, or other pharmaceuticals as well as lifestyle and behavioral adjustments. However, if patients do not adhere to the prescribed regimen they experience exacerbations of their asthma symptoms, which in turn are associated with more frequent use of a short-acting beta-agonist (SABA) "rescue" inhaler.

Figure 5B:
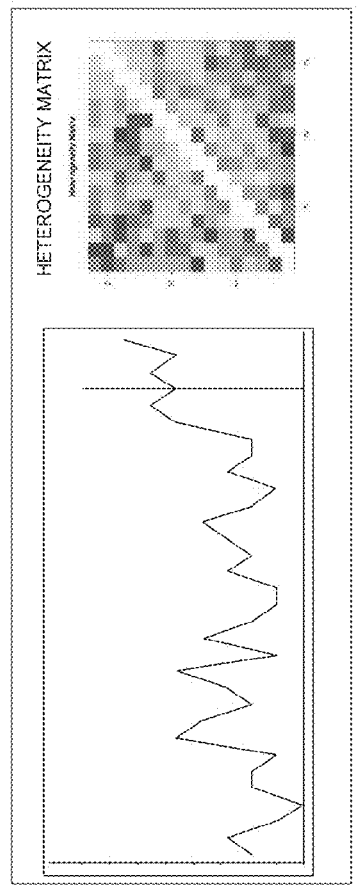

In some embodiments, a medical device may directly and/or indirectly provide an EHR, such as session logging system 160, with recorded information. For example, increasingly, sensor- and telecommunications-equipped inhaler devices are being used to characterize the respiratory status of asthma patients. In this example embodiment actually reduced to practice, daily counts of rescue inhaler use were recorded by a Bluetooth-enabled digital inhaler device (manufactured by Propeller Health Inc.). A timeseries of logged events (daily counts) was obtained that comprised of 32 or more date-time stamped values of such daily inhaler-use counts were collected. FIG. 5A depicts a graph of the timeseries. From this timeseries, SSA change-point detection models were constructed. Despite wide variations in daily inhaler-use counts during periods of "stable" asthma symptoms, SSA determinations of change-point were able to accurately detect the onset of non-adherence that produced exacerbations of asthmatic symptoms. FIG. 5B depicts the heterogeneity matrix determined from this example and also shows a redline indicating a change-point in the timeseries.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and sub-combinations are of utility and may be employed without reference to other features and sub-combinations and are contemplated within the scope of the claims. Not all steps listed in the various figures need be carried out in the specific order described. Accordingly, the scope of the invention is intended to be limited only by the following claims.

What is claimed is:

1. A method for developing a predictive model configured for predicting the likelihood of non-adherence for an individual target subject, the method comprising:
receiving, by a data communication controller, information for a target subject, from a system that logs adherence to attendance of the target subject at periodic visits or online sessions or from third-party agencies;
generating, based on at least the information for the target subject, a timeseries of historical activity, wherein random noise comprising Gaussian noise is added to the timeseries;
analyzing, the timeseries by computing a statistical relationship between the timeseries and an outcome of a singular spectrum analysis (SSA) computation of attendance information from the target subject to produce an analysis result, wherein the SSA computation is performed with column and row projector centering;
calculating a possibility of non-adherence for the target subject based on the analysis result and comparison of the result to a decision threshold; and
communicating an alert to a case manager assigned to the target subject where the possibility of non-adherence exceeds the decision threshold.

2. The method of claim 1, wherein the method further comprises:
comparing the possibility of non-adherence with a previously determined possibility of non-adherence for the target subject where the possibility of non-adherence does not exceed the decision threshold; and
communicating the alert to the case manager where a discrepancy between the possibility of non-adherence and the previously determined possibility of non-adherence indicates an increase in the possibility of non-adherence.

3. The method of claim 1, wherein the method further comprises:
comparing the possibility of non-adherence with a previously determined possibility of non-adherence for the target subject where the possibility of non-adherence does not exceed the decision threshold; and
sending a notification to the case manager where no discrepancy exists between the possibility of non-adherence and the previously determined possibility of non-adherence.

4. The method of claim 1, further comprising sending an alert to the case manager if the expected log status of adherent attendance or appearance or participation is not received at a scheduled interval.

5. The method of claim 1, wherein the system logs adherence to attendance of the target subject from the third-party agencies, and the third-party agencies comprise at least one of a health services provider, a law enforcement agency, a school, a social services agency, a religious services organization, a club, or a society.

6. The method of claim 1, wherein the system logs adherence to attendance of the target subject from the third-party agencies, and the information for the target subject from the third-party agencies comprises at least one of following: past health records, criminal records, employment status, school enrollment, housing status, participation status in health coaching, training or rehabilitation programs, and substance use.

7. The method of claim 1, wherein the timeseries is comprised of binomial, multinomial, or ordinal values, and wherein at least one value denotes non-adherence, absconding, relapse, or recidivism.

8. The method of claim 1, wherein the time dimension of the timeseries is one of (a) continuous actual date-time; (b) coarsened continuous date-time; (c) transformed continuous time; and (d) discrete serial occurrences indexed in sequence of occurrence.

9. One or more computer storage media storing computer-useable instruction that, when implemented on a computing device, cause the computing device to perform operations, the operations comprising:
receiving session log data, wherein the session log data comprises at least an indication of a target subject's performance of prescribed program events;
generating, based on at least the session log data, a timeseries of historical activity, wherein random noise comprising Gaussian noise is added to the timeseries;
analyzing the timeseries by computing a statistical relationship between the timeseries and an outcome of a singular spectrum analysis (SSA) computation to produce an analysis result wherein the SSA computation is performed with column- and row-projector centering;
generating a possibility value for the target subject based on the analysis result;
determining the possibility value satisfies a decision threshold; and
in response to the possibility value exceeding the decision threshold, sending an alert to a case manager assigned to the target subject, wherein the alert comprises at least an indication of a high possibility of relapse, recidivism, non-adherence, or absconding for the target subject.

10. The computer storage media of claim 9, wherein analyzing the timeseries further comprises a Markov dynamic programming computation, a CUSUM computation, Bayesian quickest detection computation, a Lorden's test, a Page's test, a hierarchical divisive estimation computation, or a group-fused Lasso computation.

11. The computer storage media of claim 10, wherein the input variables comprise the timeseries and at least one of a decision threshold (P); an offset; a noise amplitude; a window length (L); a base series length (B); and a neighborhood size.

12. The computer storage media of claim 11, wherein the input variables comprise the window length L and L is a fraction of a length of the timeseries (Λ), or the input variables comprise the base series length B and B is a fraction of a length of the timeseries (Λ).

13. The computer storage media of claim 12 wherein the fraction of Λ is between 0.2*Λ and 0.5*Λ.

14. The computer storage media of claim 11, wherein the input variables comprise the neighborhood size, and the neighborhood size is a fraction of L between 0.2*L and 0.5*L.

15. The computer storage media of claim 10, wherein the SSA computation produces a heterogeneity matrix (Hankel matrix) and Hankel matrix factor vector.

16. The computer storage media of claim 10, wherein the notification further comprises a recommendation for at least one of:
    altering the target subject's prescribed program events;
    reserving resources, for the target subject, in a care facility associated with treatment and/or management of the consequences of potential non-adherence;
    ordering increased monitoring of the target subject; and
    ordering increased testing of the individual; and/or ordering prescriptions for the patient.

17. A system for predicative intervention, the system comprising:
    a target monitoring device for determining adherence information for a target subject, the adherence information associated with prescribed program events;
    one or more processors;
    computer readable media having computer-executable instructions stored thereon which, when executed by the one or more processors, cause the one or more processors to:
    receive adherence information for the target subject;
    generate, based on the adherence information for the target subject, a timeseries of historical performance of prescribed program events, wherein random noise comprising Gaussian noise is added to the timeseries;
    generate, based on the timeseries, a possibility value by computing a statistical relationship between a set of input variables and an outcome of a singular spectrum analysis (SSA) computation, wherein the SSA computation is performed with column- and row-projector centering;
    compare the possibility value with a decision threshold;
    in response to the possibility value satisfying the decision threshold, send an alert to a case manager assigned to the target subject, wherein the alert comprises at least an indication of a high possibility of relapse, recidivism, non-adherence, or absconding for the target subject.

18. The system of claim 17, wherein the timeseries is comprised of binomial, multinomial, or ordinal values, and wherein at least one value denotes non-adherence, absconding, relapse, or recidivism.

* * * * *